(12) United States Patent
Pfefferle et al.

(10) Patent No.: US 8,366,751 B2
(45) Date of Patent: Feb. 5, 2013

(54) BONE PLATE HAVING ELEVATIONS PERMITTING COUNTERSINKING OF BONE SCREWS

(75) Inventors: Joachim Pfefferle, Munstertal (DE); Dirk Thiel, Staufen (DE); Carl-Peter Cornelius, Ulm (DE)

(73) Assignee: Medartis AG, Basel (CH)

( * ) Notice: Subject to any disclaimer, the term of this patent is extended or adjusted under 35 U.S.C. 154(b) by 946 days.

(21) Appl. No.: 11/849,022

(22) Filed: Aug. 31, 2007

(65) Prior Publication Data
US 2008/0015593 A1    Jan. 17, 2008

(30) Foreign Application Priority Data
Mar. 24, 2005  (CH) .......................... 517/05
Mar. 20, 2006  (WO) ................ PCT/CH2006/000163

(51) Int. Cl.
*A61B 17/80* (2006.01)
(52) U.S. Cl. ...................... 606/286; 606/280
(58) Field of Classification Search ............. 606/70–71, 606/280–299, 902–906; 623/17.15, 17.17–17.18
See application file for complete search history.

(56) References Cited

U.S. PATENT DOCUMENTS

| | | | | |
|---|---|---|---|---|
| 4,408,601 A * | 10/1983 | Wenk | ........................ | 606/282 |
| 5,558,674 A * | 9/1996 | Heggeness et al. | ........... | 606/278 |
| 5,690,631 A | 11/1997 | Duncan | | |
| 5,807,396 A * | 9/1998 | Raveh | ........................ | 606/287 |
| 6,077,266 A * | 6/2000 | Medoff | ........................ | 606/281 |
| 6,322,562 B1 * | 11/2001 | Wolter | ........................ | 606/62 |
| 6,695,845 B2 * | 2/2004 | Dixon et al. | ................ | 606/70 |
| 6,730,091 B1 * | 5/2004 | Pfefferle et al. | ............. | 606/70 |
| 6,786,909 B1 | 9/2004 | Dransfeld et al. | | |
| 6,955,677 B2 * | 10/2005 | Dahners | ........................ | 606/287 |
| 6,960,211 B1 * | 11/2005 | Pfefferle et al. | ............. | 606/282 |
| 6,974,461 B1 * | 12/2005 | Wolter | ........................ | 606/283 |
| 2001/0021851 A1 * | 9/2001 | Eberlein et al. | ............. | 606/69 |
| 2006/0235400 A1 * | 10/2006 | Schneider | ................ | 606/69 |

FOREIGN PATENT DOCUMENTS

| | | |
|---|---|---|
| FR | 742 618 | 3/1933 |
| WO | WO 95/16403 | 6/1995 |
| WO | WO 00/66012 | 11/2000 |

(Continued)

OTHER PUBLICATIONS

International Search Report for International Application No. PCT/CH2006/000163 dated Jul. 4, 2006.

*Primary Examiner* — Kevin T Truong
*Assistant Examiner* — Larry E Waggle, Jr.
(74) *Attorney, Agent, or Firm* — Brinks Hofer Gilson & Lione

(57) ABSTRACT

A bone plate has at least one plate hole whose hole axis runs obliquely in relation to the underside of the plate. The hole axis has an elevation angle ($\epsilon$) in relation to the plane of the underside of the plate which is different from 90°, and in which plate the upper face of the plate runs at least partially not parallel to the underside of the plate, at least in the area around the plate hole, but instead runs at a right angle to the hole axis. The plate hole is designed such that a bone screw, which is screwed into the plate hole, can be blocked in the plate hole at an angle selected from a predefined angle range around the elevation angle ($\epsilon$) of the hole axis of the plate hole only by cooperation of the plate hole with the bone screw, without other additional auxiliary means.

12 Claims, 10 Drawing Sheets

FOREIGN PATENT DOCUMENTS

| WO | WO 01/19268 | 3/2001 |
| WO | WO 01/30251 | 5/2001 |
| WO | WO 2004/086990 | 10/2004 |
| WO | WO 2005018472 A1 * | 3/2005 |

* cited by examiner

BONE PLATE HAVING ELEVATIONS PERMITTING COUNTERSINKING OF BONE SCREWS

CROSS REFERENCE TO RELATED APPLICATIONS

This application claims the benefit of priority from International Patent Application Serial No. PCT/CH2006/000163, filed on Mar. 20, 2006, entitled Bone Plate which claims priority from Swiss Patent Application Serial No. 517/05, filed on Mar. 24, 2005. Application Serial Nos. PCT/CH2006/000163 and 517/05 are hereby incorporated by reference in their entirety.

BACKGROUND

The invention relates to an apparatus for securing bones, and in particular, to a bone plate.

Bone plates are being used today in countless different embodiments and offer a form of assistance in osteosynthesis that has become indispensable, in particular in treating fractures where the two bone fragments on the proximal and distal sides of a fracture must become fused again. The bone plate serves to hold the bone fragments in the desired position in relation to one another so that the bone can become fused again as desired.

A special example of such a bone plate is known from WO-A-01/19268. In individual embodiments of the bone plate described there (see FIG. 2 and FIG. 3 in WO-A-01/19268), the hole axis of individual holes in the plate runs obliquely in relation to the underside of the plate while the upper face of the plate and the underside of the plate run parallel to one another. The inside wall of the plate hole has a peripheral burr which becomes deformed when the bone screw is screwed into the hole so that the screw becomes "blocked" in the plate hole, i.e., is secured in its tightened position.

The bone plates described in WO-A-01/19268 are disclosed specifically for tubular bones such as the tibia. Such bone plates have a great material thickness, so normally it does not present any problem to countersink the head of the screw in the screw hole even when the screw is tightened so that the actual direction of tightening deviates from the "ideal direction of tightening," i.e., the direction of the hole axis, which is possible within certain limits. In addition, in the case of tubular bones such as the tibia, the operating field is usually readily accessible for the surgeon.

It proves to be more difficult to countersink the screw head in "thin" bone plates having a much smaller plate thickness, namely in particular when the actual direction of tightening the bone screw deviates from the "ideal direction of tightening" because then due to the smaller plate thickness the axial length of the hole is not very great. However, such comparatively "thin" bone plates are the rule due to the small amount of soft tissue available and also for aesthetic reasons, especially in the maxillofacial area.

WO-A-95/16403 discloses a bone plate in which the axes of the holes in the plate run at an angle different from 90° in relation to the plane of the underside of the plate. An elevation is provided on the upper face of the plate around each plate hole. To fasten the bone plate, a pilot hole is first created with a suitable drilling tool, which is guided into the oblique plate hole, so that the pilot hole runs precisely in the direction of the hole axis. In the subsequent tightening of the bone screw, the bone screw is guided in the pilot hole and is tightened in the ideal direction of tightening, namely in the direction of the hole axis. The cylindrical screw head can therefore be accommodated completely in the elevation in the bone plate. A type of blocking of the bone screw in the position in which it is completely screwed in is proposed here in such a way that recesses are provided in the outside wall of the cylindrical screw head and after the screws have been screwed in completely, the elevation in the bone plate is completely deformed into these recesses with the help of a suitable tool. However, the bone screw can be screwed in only exactly in the direction of the hole axis in the case of the bone plate known from WO-A-95/16403 because otherwise the cylindrical screw head cannot be accommodated in the elevation. Therefore, a pilot hole must also be created in the bone, guiding the desired direction of screwing in the screw precisely. However, this is complex and tedious for the surgeon (creating the pilot hole, etc.) and also in practical terms does not allow any deviation in the direction of tightening from the ideal direction of tightening.

However, the surgeon is frequently confronted with the problem of being unable to easily recognize the "ideal tightening direction" in the case of hole axes running obliquely and thus an oblique "ideal tightening direction" —especially when the surgical field is cramped. If the actual tightening direction of the bone screw from the ideal tightening direction deviates to a certain extent, the screw head could not be countersunk in the plate hole when using the bone plate described above. However, predrilling a pilot hole in the ideal direction of tightening is complicated and expensive and is especially problematical in terms of accessibility in the maxillofacial area. However, without a pilot hole, there is the problem for the surgeon of being able to recognize the "ideal tightening direction" easily, in particular when interoral access (access only through the mouth) is to be performed, but this can also occur in a case of access with a skin incision. The location of the skin incision cannot be selected at random due to the distribution of nerves in the maxillofacial area, so the screwdriver can then be guided at a right angle through the incision and will then encounter the bone plate. This would be a simple variant in terms of handling but it is often impossible to implement because of the distribution of the nerves. The same difficulty in selecting the location also occurs with a so-called "transbuccal" access in which a small hole is made through the skin (but not a large incision) and then the screwdriver is passed through this hole, for example. However, the plate itself may be introduced interorally and held at the desired location.

SUMMARY

Specifically, the upper face of the plate of the inventive bone plate does not run parallel to the underside of the plate to at least some extent in the area around the plate hole but instead runs at a right angle to the hole axis. This surface makes it possible for the surgeon to better recognize the ideal direction of tightening of the bone screw and thus to screw in the screw at least approximately in the ideal direction of screwing, so it is possible in most cases to countersink the screw head completely or almost completely in the plate hole. The plate hole is designed so that a bone screw, which is screwed into the plate hole, can be blocked in the plate hole at an angle from a predefined angle range about the angle of elevation of the hole axis in the plate, and this can be accomplished only through the cooperation of the specially designed plate hole with the bone screw, i.e., without additional further auxiliary means. This means that the surgeon need not drill a pilot hole when inserting the bone screw, which is frequently also difficult in terms of accessibility, especially in the maxillofacial area. Furthermore, when the bone screw is screwed in, the bone plate allows a certain range of variation around the ideal angle of tightening, which is advantageous inasmuch as, first of all, it is difficult to tighten a screw precisely in the ideal direction of tightening without drilling a pilot hole while on the other hand, the available bone material in a patient is often such that the screw can be secured better in the bone at an angle that differs from the ideal angle of tightening. With the bone plate according to this invention, interoral access in particular is facilitated, which makes it possible to omit the skin incision in many cases. Once the screw has been tightened, no special measures are needed to block it in place, which is why the respective plate hole is designed so that the blocking comes about only through the interaction of the specially designed plate hole with the bone screw, i.e., without further auxiliary means (such as spreading screws which spread the screw head, or separate covers which must then be screwed in place to hold down the screw head).

In an advantageous exemplary embodiment of the bone plate according to the invention, the predefined angle range about the elevation angle of the hole axis may amount to approximately 15°.

An exemplary embodiment of the bone plate according to the invention comprises multiple plate holes whose hole axis runs obliquely in relation to the underside of the plate in each case, whereby both the angle of elevation of the hole axis and the azimuth angle, i.e., the rotational angle, in the plane of the underside of the plate can be determined individually for each individual plate hole. This is advantageous in particular for bone plates for the maxillofacial area, specifically for the interoral access discussed previously, or for access with a skin incision (because of the lack of free choice of the site of the skin incision) or for a transbuccal access. Due to the possibility of individual determination of the elevation angle and the azimuth angle, the orientation of the individual axes of the holes in the bone plate may be such that an interoral access, access with a skin incision or transbuccal access to all plate holes is possible, depending on the particular application. It is thus also possible in particular to produce bone plates which are tailored to very specific applications, e.g., bone plates for mandibular fractures or collum fractures. At the same time, the surgeon may readily recognize the particular ideal direction of tightening for the screw based on the inclined surface on the upper face of the plate, which is at a 90° angle to the respective hole axis.

Another advantageous exemplary embodiment of the bone plate according to the invention has at least partially an elevated area in the area around the respective plate hole with the hole axis running obliquely in relation to the underside of the plate. The elevation is arranged with respect to the particular plate hole so that the head of a bone screw, which can be screwed into the plate hole, can be countersunk in the corresponding plate hole. This should mean that the elevation is arranged so that in the case of a typical access selected for a certain operation, the surgeon can recognize on the one hand the ideal direction of tightening of the screw on the basis of the surface running at a right angle to the hole axis (and thus to the ideal direction of tightening) near the plate hole on the upper face of the plate, while on the other hand, the screw can be countersunk completely in the plate hole when it is tightened. The hole axis running at a right angle to the underside of the plate on the one hand and the elevation on the upper face of the plate on the other hand make it possible to screw in a screw relative to the underside of the plate at a considerable inclination in relation to the normal to the underside of the plate and nevertheless to completely countersink the screw into the plate hole. For example, if it is assumed that the hole axis is inclined by an angle of 20° with respect to the normal and if it is further assumed that the embodiment of the plate hole allows the screw to be inclined by ±15° in relation to the ideal direction of tightening (which is already inclined by 20° with respect to the normal) while nevertheless countersinking the screw completely in the plate hole and optionally being able to block it there (see WO 2004/086990, for example), this yields a maximum angle of 20°+15°=35° with respect to the normal. This opens up considerable advantages to the surgeon for screwing the screw into the plate.

In a refinement of the bone plate according to the invention, the bone plate has multiple plate holes with an elevation on the upper face of the plate, wherein the elevations are designed and arranged individually on each plate hole having an elevation. Although it would be possible in principle to design and arrange the elevation, the hole axes and the surfaces running at a right angle to the hole axes on the upper face of the plate identically, an individual design of the elevation for each individual plate hole allows an optimized design of the bone plate for the particular location of use.

An advantageous exemplary embodiment of the bone plate according to the invention has several eyes and webs through which the eyes are interconnected. In the area of one or more eyes, the plate has an elevation but not in the area of the webs between the eyes. The plate is thus sufficiently flexible in the area of the webs to be able to even interoperatively bend it to optimally fit the bone.

As mentioned previously, in an advantageous exemplary embodiment of the bone plate according to the invention, all the plate holes are designed so that all the bone screws can be screwed interorally during fixation of the plate with the help of the bone screws. This makes it possible to avoid a skin incision, even when virtually the entire mandible must be covered by one bone plate, for example.

As already mentioned, the inventive bone plate mentioned above is especially suitable for applications in the maxillofacial area. The thickness of the material of such bone plates is in the range of 0.5 mm to 2.5 mm, in particular in the range of 0.5 mm to 1.6 mm (this refers to the general thickness of the material of the bone plate, not the thickness of the material in an elevated area). However, the present invention is by no means limited to such relatively "thin" bone plates, which are used in the maxillofacial area. Instead, it is also possible to produce the inventive bone plates having a greater material thickness (e.g., up to a material thickness of 6 mm), which may then be used in the field of orthopedics, for example (limbs, spine, pelvis, etc.), where more massive bone plates are often required.

In another exemplary embodiment of the bone plate according to the invention, the inside wall of the plate hole(s) is/are provided with a blocking contour which cooperates with a bone screw that can be screwed into the plate hole in such a way that it can be blocked in the plate hole. This allows an angularly stable securing of the bone screw in the plate hole. Examples of such a blocking contour include the peripheral burr disclosed in WO-A-01/19268 or blocking contours such as those disclosed in WO-A-00/66012.

In a special exemplary embodiment of the bone plate according to the invention, the blocking contour on the inside wall of the plate hole is designed so that a bone screw that can be screwed into the plate hole and has a suitably designed clamping surface on the screw head can be blocked in the plate hole by blocking the screw head with the blocking contour. Such a blocking contour is described, for example, in WO-A-2004/086990.

The inventive bone plate is preferably manufactured from a biocompatible material, e.g., titanium or a titanium alloy. The biocompatible material may also be a bioabsorbable material, e.g., HA/PLLA (hydroxyapatite/poly-(L-lactic acid); PLLA/PGA (poly-(L-lactic acid)/polyglycolic acid); PLLA/PDLLA/TMC (poly-(L-lactic acid)/poly-(D,L-lactic acid)/trimethylenecarbonate); PLLA/PDLLA (poly(L-lactic acid)/poly-(D,L-lactic acid)).

BRIEF DESCRIPTION OF THE DRAWINGS

Other advantageous aspects are derived from the following description of exemplary embodiments of the bone plate according to the invention with the help of drawings, in which.

DETAILED DESCRIPTION

Figure 1:
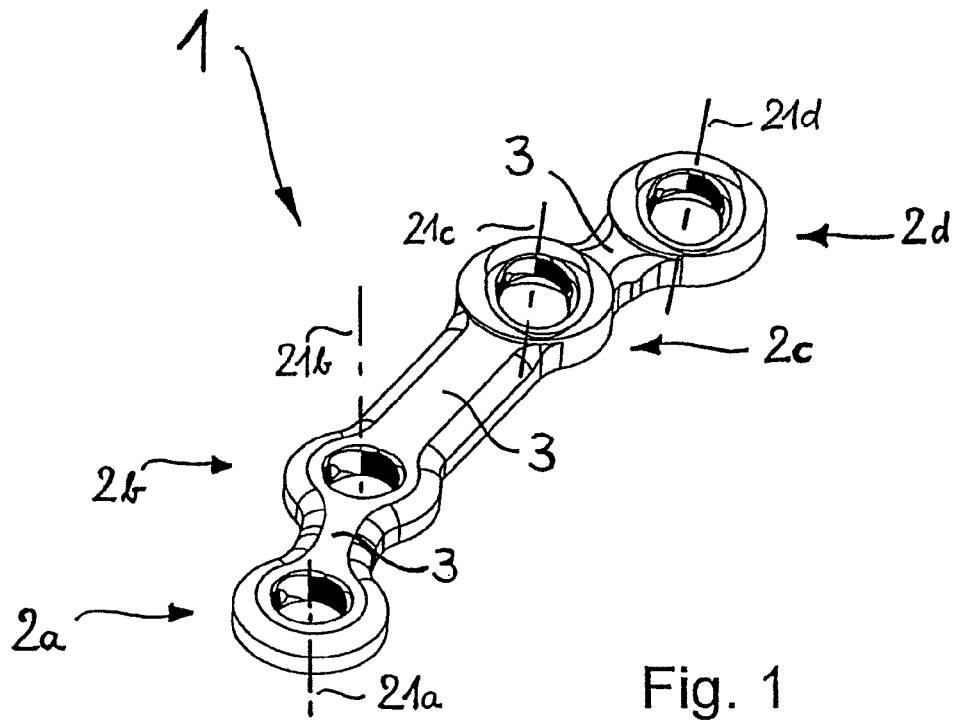
FIG. 1 shows a first exemplary embodiment of the bone plate according to the invention in a perspective view.
Figure 2:
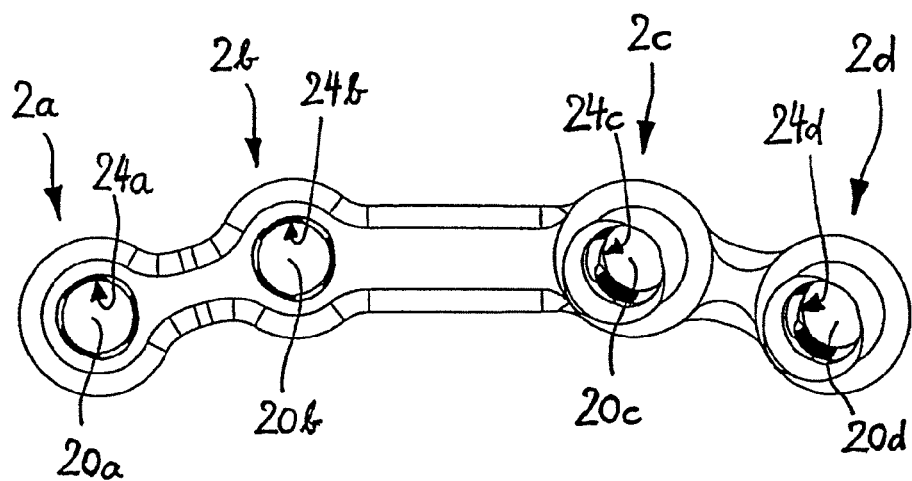
FIG. 2 shows the bone plate from FIG. 1 in a top view.
Figure 3:
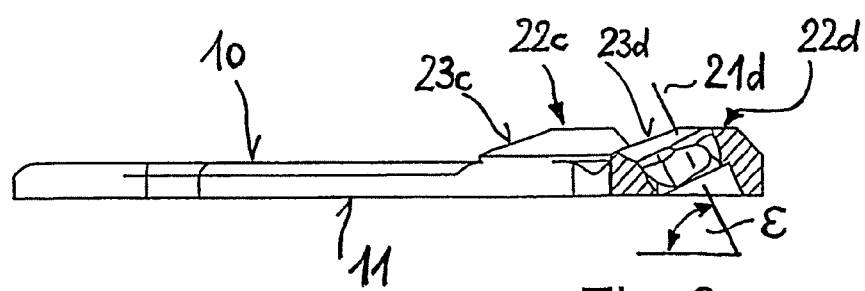
FIG. 3 shows the bone plate from FIG. 1 in a side view, showing one eye in cross section.

FIG. 1, FIG. 2 and FIG. 3 show a first exemplary embodiment of a bone plate 1 according to the invention. The bone plate 1 has a plate upper face 10 and a plate underside 11 (see FIG. 3). It also includes four eyes 2a, 2b, 2c and 2d, all eyes being interconnected by webs 3. Plate holes 2a through 2d are provided in the eyes 2a-2d, so that bone screws can be screwed through these plate holes from the upper face 10 of the plate into the bone underneath. This is explained in greater detail below.

The web 3 situated between the two inner eyes 2b and 2c is designed to be more massive than the webs between the eyes 2a, 2b and/or 2c, 2d. Thus more massive web 3 comes to lie above the fracture in fixation of the bone plate to the bone in treating a fracture (to be explained below) and thereby stabilizes the fracture, while the plate can be bent to better conform to the bone in the area of the two outer eyes 2a, 2d because of the thinner web there.

It can also be seen readily (FIG. 1) that the hole axes 21a and 21b of the plate holes 20a and 20b run at a right angle to the underside of the plate (and also at a right angle to the upper face of the plate, which runs parallel there) while this is not the case for the hole axes 21c and 21d of the plate holes 20c and 20d. Since the respective hole axis always at the same time also indicates the "ideal direction of tightening" for a bone screw, the ideal direction of tightening for the screws in the plate holes 20c and 20d also runs obliquely to the underside 11 of the plate. This is seen especially well on the example of the hole axis 21d in FIG. 3 which forms an angle ϵ of elevation with the plane of the underside 11 of the plate (the plane of the underside 11 of the plate runs at a right angle to the plane of the paper in FIG. 3). In addition, it is also possible to select the azimuth angle of the hole axis, i.e., the rotational angle within the plane of the underside 11 of the plate according to the intended purpose of a bone plate (i.e., instead of running obliquely from the upper left to the lower right as shown in FIG. 3, the hole axis 21d could also run obliquely from the upper right to the lower left, which would correspond to an azimuth angle difference of 180°). This is essentially possible for each individual plate hole, but is implemented here only with two plate holes, namely with plate holes 20c and 20d, which may be dependent on the particular intended purpose of use of the bone plate.

In addition, it can be seen that in the area around the two plate holes 20c and/or 20d, i.e., around the plate holes with the hole axes 21c and/or 21d running obliquely, an elevation 22c and/or 22d is provided on the upper face 10 of the plate. The elevation may also be designed and arranged individually at each plate hole. The elevation ensures that the screw head of a bone screw can be accommodated such that it is completely countersunk when screwed into the bone plate in the ideal direction of tightening or almost in this direction, despite the small thickness of material of the bone plate, which will typically have a material thickness in the range of 0.5 mm to 2.5 mm, preferably in the range of 0.5 mm to 1.6 mm, for bone plates for use in the maxillofacial area (see, for example, FIG. 5, bone screw at the far right).

In addition, it can be seen that the upper face of the plate runs at least partially not parallel to the underside of the plate in the area around the plate hole 20c and/or 20d. This is true in particular for the (partial) area 23c and/or 23d running at a right angle to the hole axis 21c and/or 21d. This area 23c and/or 23d is useful for the surgeon during fixation of the bone plate because it indicates the ideal direction of tightening. It is thus much easier for the surgeon to recognize the ideal direction of tightening even in a cramped operating field and to tighten the screw accordingly.

Finally, one can also see that the inside wall of the individual plate holes 20a-20d is provided with a blocking contour 24a-24d (see FIG. 2) which makes it possible to block the screw head of a special bone screw having a blocking contour in the plate hole. The blocking contour can be seen even better in FIG. 3—both the blocking contour as well as the respective screw head which is designed accordingly are, however, known in principle from WO-A-2004/086990, the disclosure of which in this regard is herewith incorporated. Therefore, no further description of the blocking contour or the respective clamping surface on the screw head is necessary.

Figure 4:
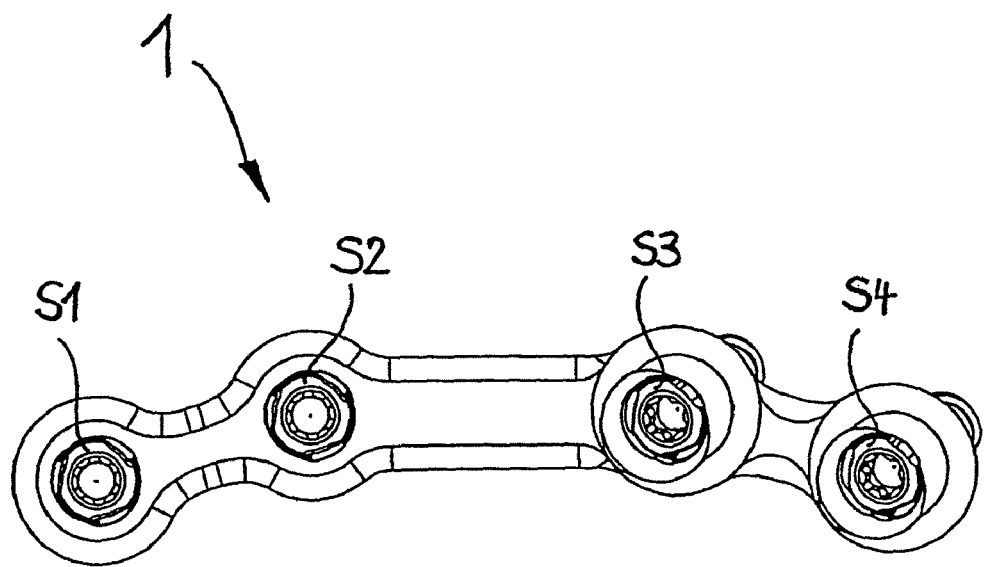
FIG. 4 shows the bone plate from FIG. 1 with the bone screws inserted, in a top view.

FIG. 4 shows the bone plate 1 from FIG. 1, although with the bone screws S1, S2, S3 and S4 inserted, whereby the bone screws S1 through S4 have been inserted into the plate holes in the ideal direction of tightening. From the top view of FIG.

4 it can be seen that the hole axes of the two right plate holes deviate from a direction perpendicular to the underside of the plate because despite the top view of the plate, one can see the ends of the screw shaft of the bone screws S3 and S4.

Figure 5:
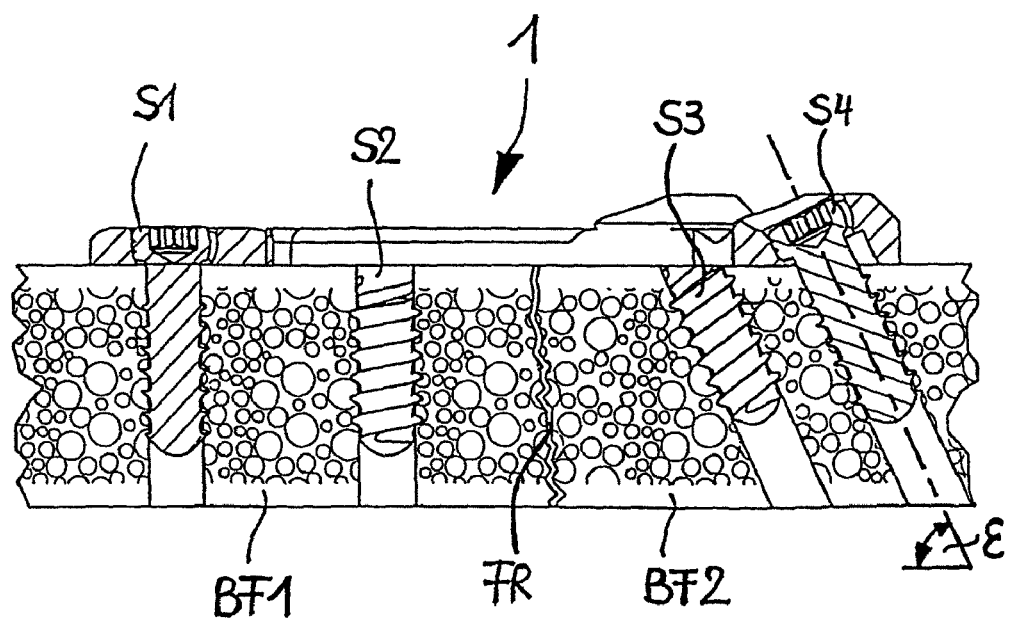
FIG. 5 shows the bone plate from FIG. 1 secured on a bone, having two eyes and screws in a sectional view.

FIG. 5 shows schematically the bone plate 1 secured to a bone with a fracture FR, or better yet it shows the bone plate 1 secured to two bone fragments BF1 and BF2, one of the two types of plate holes—a plate hole without an elevation and a plate hole with an elevation—being shown in cross section and with the bone screw S1 or S4, respectively, screwed into the bone. It can be seen here that despite screwing the bone screw S4 into the bone at elevation angle ε (the azimuth angle is disregarded here), the screw head is completely countersunk.

The advantageous engagement contour in the screw head shown in FIG. 4 and FIG. 5 for a tightening tool and the corresponding tightening tool (screwdriver) are known from DE 10 2004 026 769 A1, for example.

Figure 6:
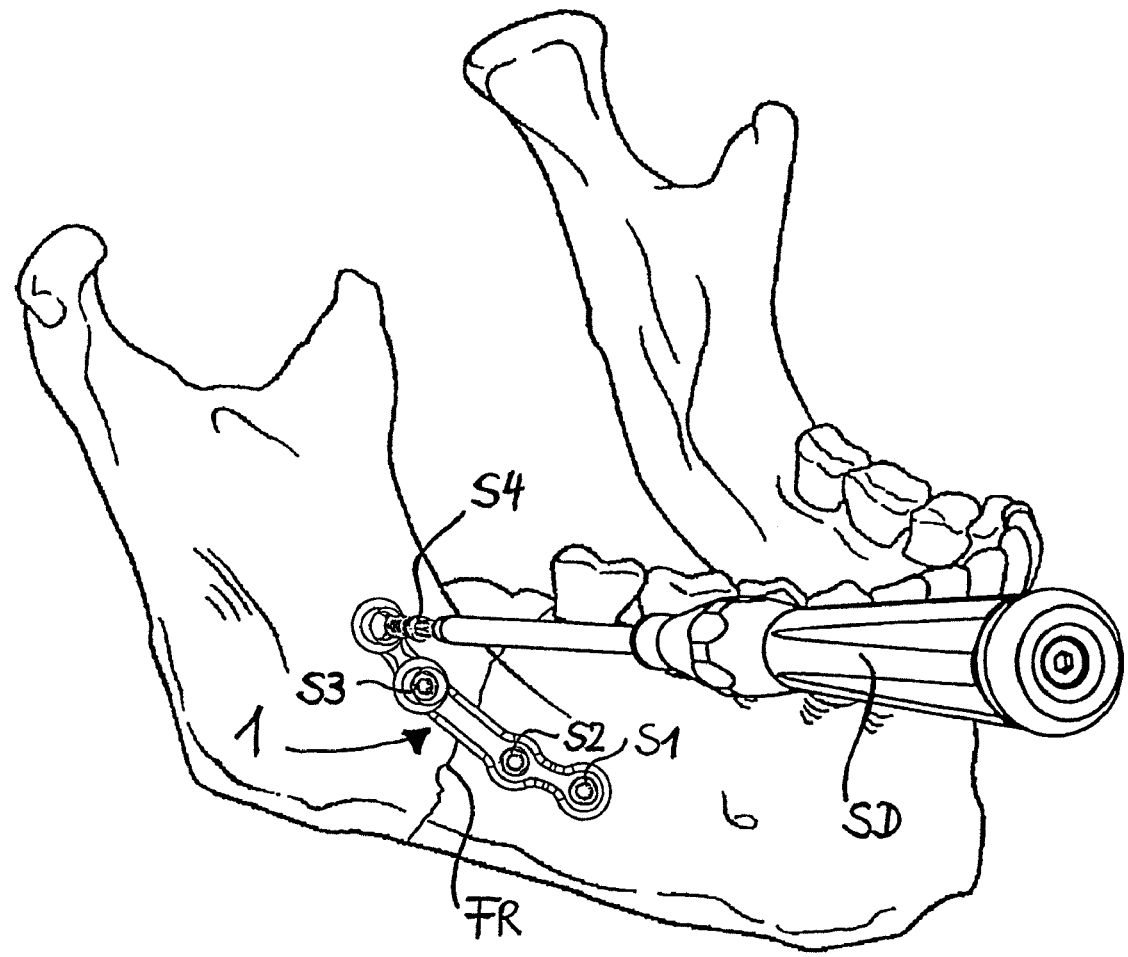
FIG. 6 shows the bone plate from FIG. 1, attached to the mandible to treat a mandibular fracture.

FIG. 6 shows the bone plate 1 in use, namely in treatment of a fracture of the angle of the mandible (mandibular fracture). While the two bone screws S1 and S2 are easily screwed into the readily accessible plate holes interorally, the particular advantage of the bone plate according to the invention can now be recognized here. The hole axes of the two plate holes which come to lie in the area of the ascending ramus mandibulae are arranged here, so that they are likewise readily accessible to the surgeon for interoral access (i.e., without a skin incision). For that reason the elevations and inclined surfaces (see explanations of FIGS. 1-3) of the two plate holes for bone screws S3 and S4 are arranged in a special manner, namely such that first of all the surgeon can recognize which is the ideal direction of tightening and on the other hand a purely interoral access is possible. This is apparent due to the spatial arrangement of the screwdriver SD which is represented symbolically for this purpose during tightening the screw S4.

Figure 7:
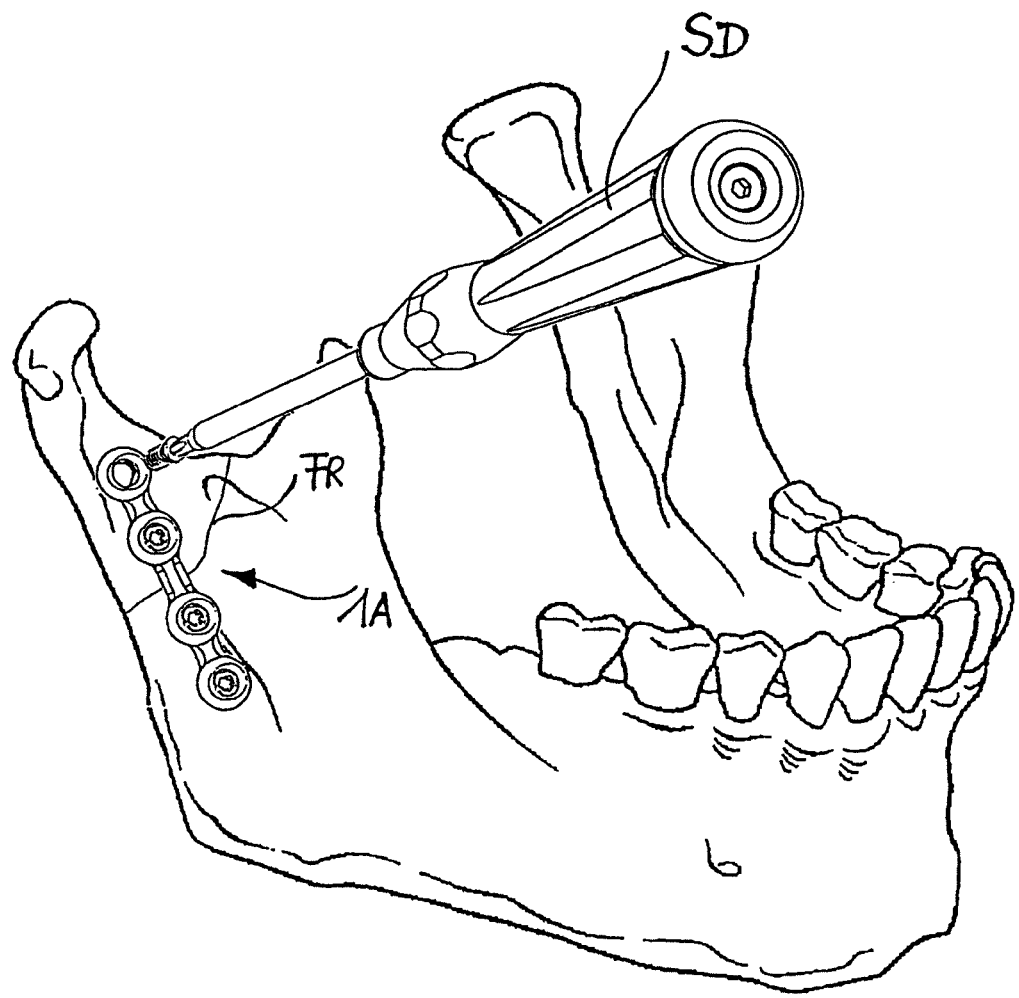
FIG. 7 shows another exemplary embodiment of a bone plate according to the invention to treat a collum fracture of the *ramus mandibulae* (interoral access)

FIG. 7 shows a second exemplary embodiment of the bone plate 1A according to the invention. The bone plate 1A differs significantly from the bone plate 1 in that it is designed to be straight and each individual plate hole is provided with an elevation. The reason for this is that the bone plate 1A—as shown in FIG. 6—is especially suitable for fractures FR in the subcondylar region of the ascending ramus mandibulae (and/or collum fractures). However, interoral access without a skin incision is possible there only to a limited extent and only when the elevations and the hole axes of the plate holes are oriented such that the screws S1 through S4 can in fact be screwed in and countersunk even with a purely interoral access in the ideal direction, and the inclined surfaces indicate to the surgeon the ideal direction of screwing in. This should become apparent again from the spatial arrangement of the screwdriver SD.

Figure 14:
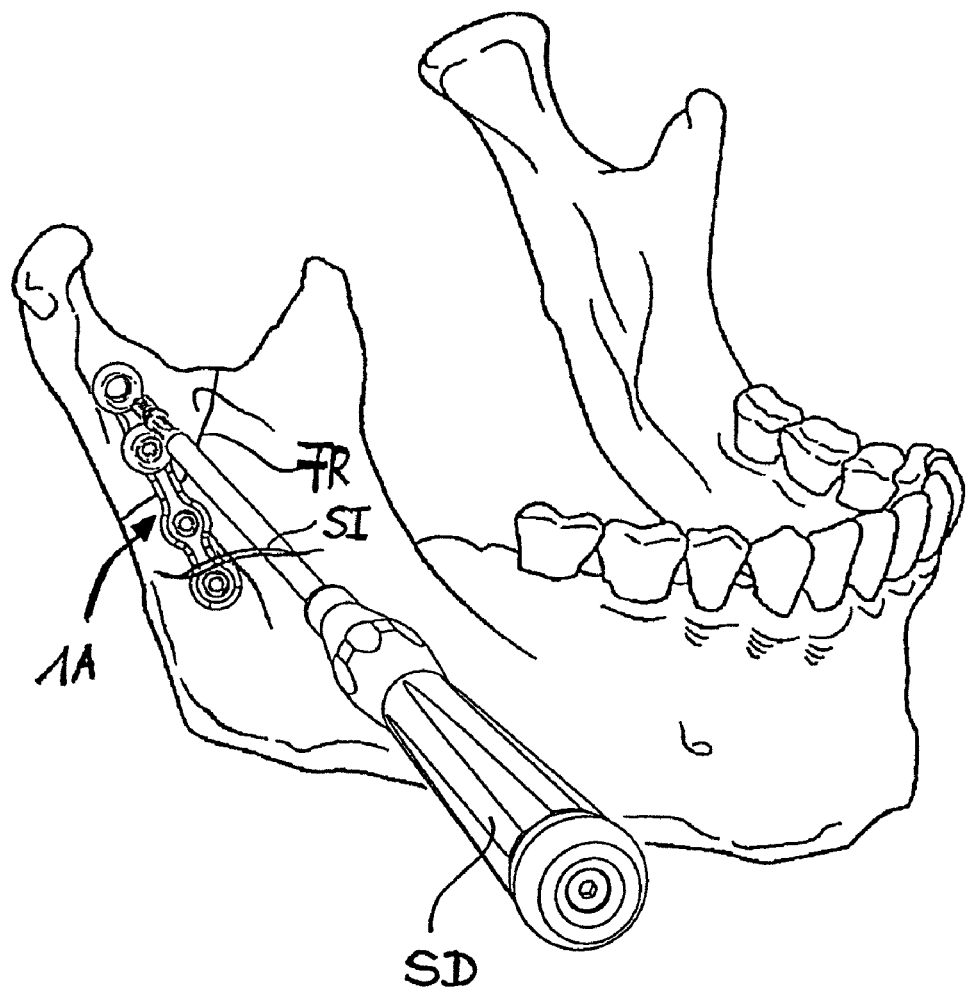
FIG. 14 shows the exemplary embodiment of the bone plate according to the invention shown in FIG. 7 (access with a skin incision).

In cases in which interoral access is impossible or cannot or should not be attempted for other reasons, access with a skin incision may be performed, for example. However, even in the case of access with an incision, the location of the skin incision cannot be simply selected at will because of the distribution of nerves in the maxillofacial area, so that the screwdriver can simply be passed perpendicularly through the incision and then strike the bone plate 1. This is expensively true for collum fractures such as those already shown in FIG. 7 (but with purely interoral access there without an incision) although this also holds for an access with skin incision S1 as shown in FIG. 14, which shows both the skin incision S1 and the screwdriver SD, so that it is possible to see from FIG. 14 that the screwdriver SD can reach the plate holes of the bone plate 1 only at an angle that differs from the normal to the plate holes of bone plate 1 in order to screw in the screws. This is also true accordingly for a transbuccal access (see further above).

Figure 8:
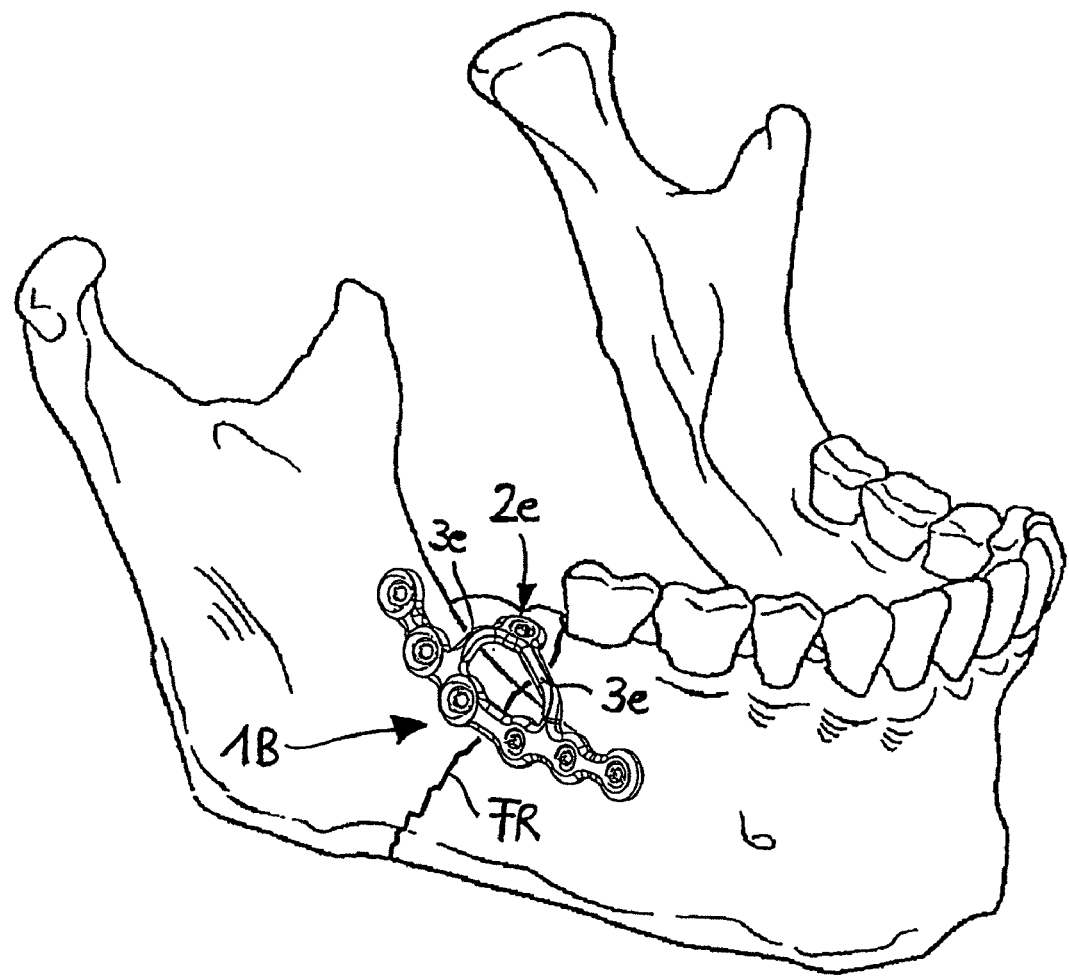
FIG. 8 shows another exemplary embodiment of a bone plate according to the invention for treatment of a mandibular fracture, showing an eye for fastening to the alveolar ridge.

FIG. 8 shows a third exemplary embodiment of the bone plate 1B according to the invention which is essentially very similar to the first exemplary embodiment of the bone plate 1 but has three plate holes without an elevation and three plate holes with an elevation for the proximal side and/or distal sides of a mandibular fracture FR. In addition, however, one eye 2e, which is also provided, can be secured to the rear end of the alveolar ridge, and there are two additional webs 3e for connecting these eyes 2e to the remaining body of the bone plate 1B. The statements made further above with regard to the orientation of the hole axes, the arrangement and design of the elevations and the ideal direction of tightening of the screw and/or the possible purely interoral access also apply accordingly.

Figure 9:
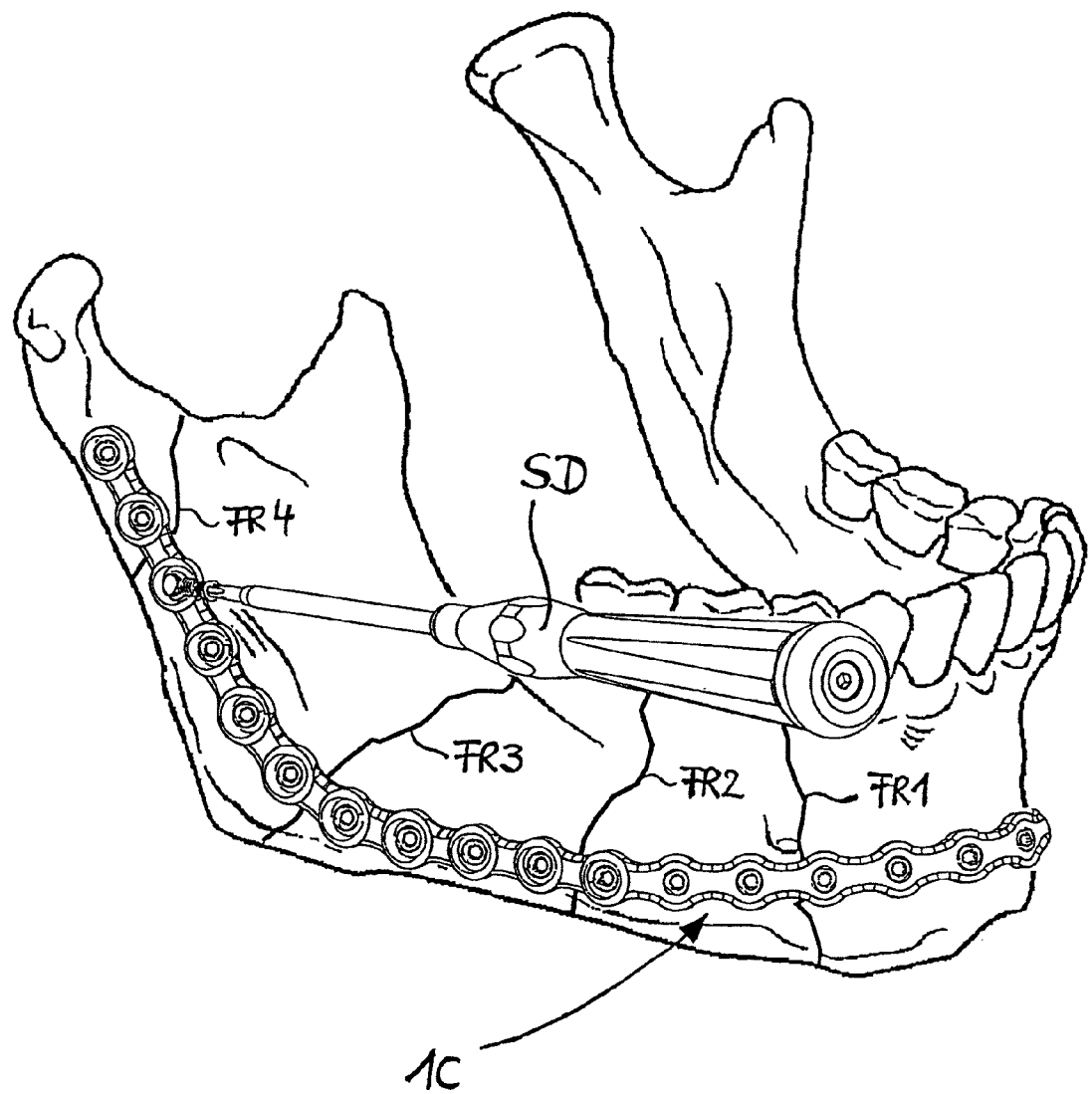
FIG. 9 shows another exemplary embodiment of a bone plate according to the invention in the form of a reconstruction plate for treating multiple fractures of the mandible.

FIG. 9 shows a fourth exemplary embodiment of the bone plate 1C according to the invention in the form of a reconstruction plate for simultaneous treatment of multiple fractures FR1, FR2, FR3, FR4 for the purpose of reconstruction of the mandible. In this exemplary embodiment, it is possible to see a plurality of eyes and webs connecting the eyes so that the plate can be bent to the desired shape as well as possible. In the front area the plate holes are designed without elevations because this area is readily accessible interorally whereas in the lateral and posterior area of the bone plate where the interoral access is more difficult, the plate holes are designed with an elevation at different angles. With respect to the orientation of the hole axes, the arrangement and design of the elevations and the ideal direction of tightening and/or the possible purely interoral access, the statements made further above apply similarly. FIG. 9 again shows a screwdriver SD for the sake of illustration.

Figure 10:
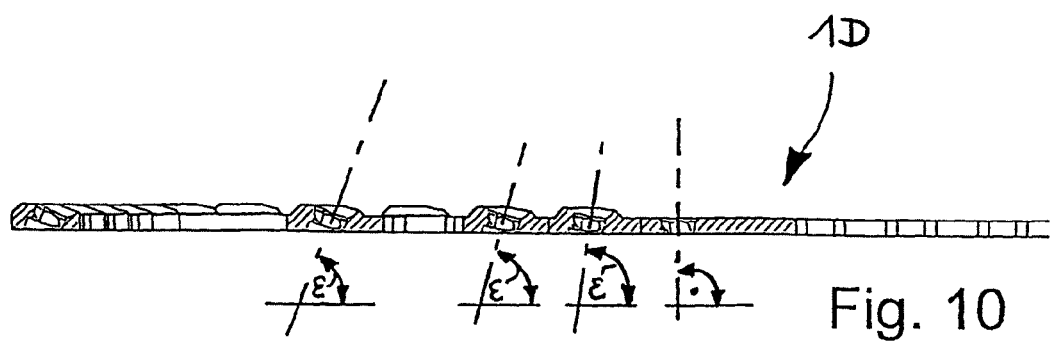
FIG. 10 shows another exemplary embodiment of a bone plate according to the invention with hole axes having various elevation angles (partially in sectional view)
Figure 11:
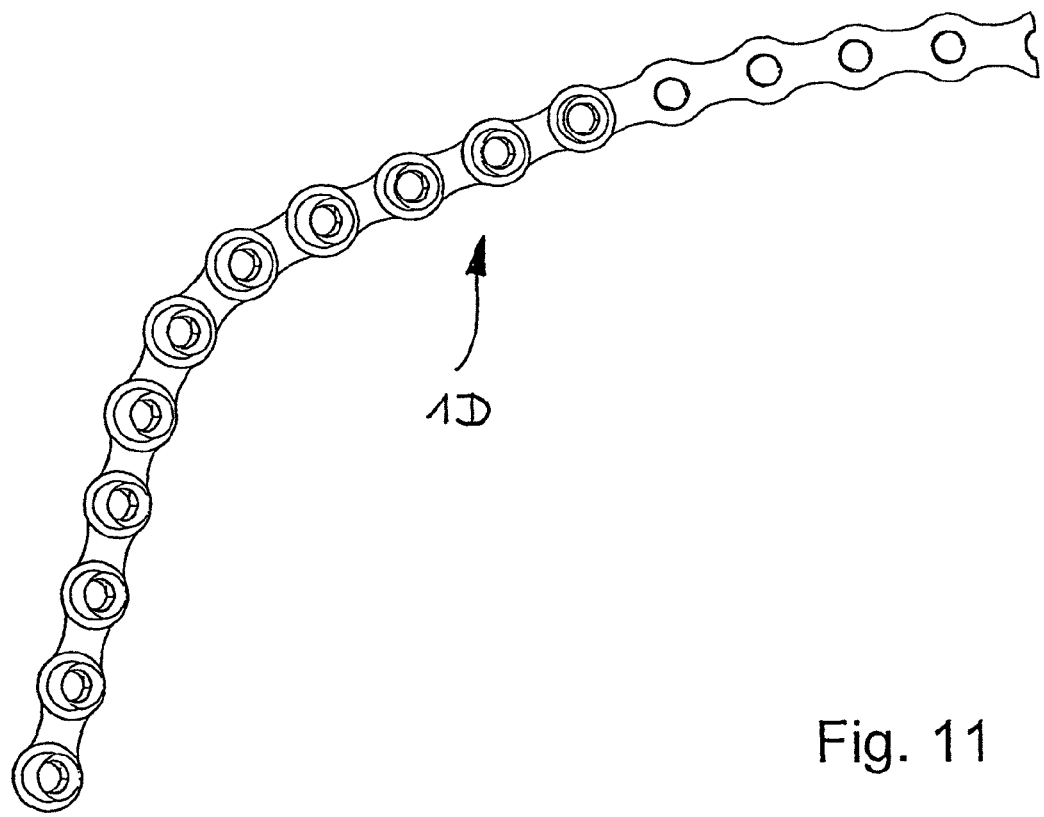
FIG. 11 shows the exemplary embodiment of the bone plate from FIG. 10 in a top view.

FIGS. 10 and 11 show another exemplary embodiment of a bone plate 1D according to the invention. In this embodiment, it can be seen in particular that the elevation angle ε of the hole axes may be different on each of the different plate holes and may in principle be determined separately for each individual hole.

Figure 12:
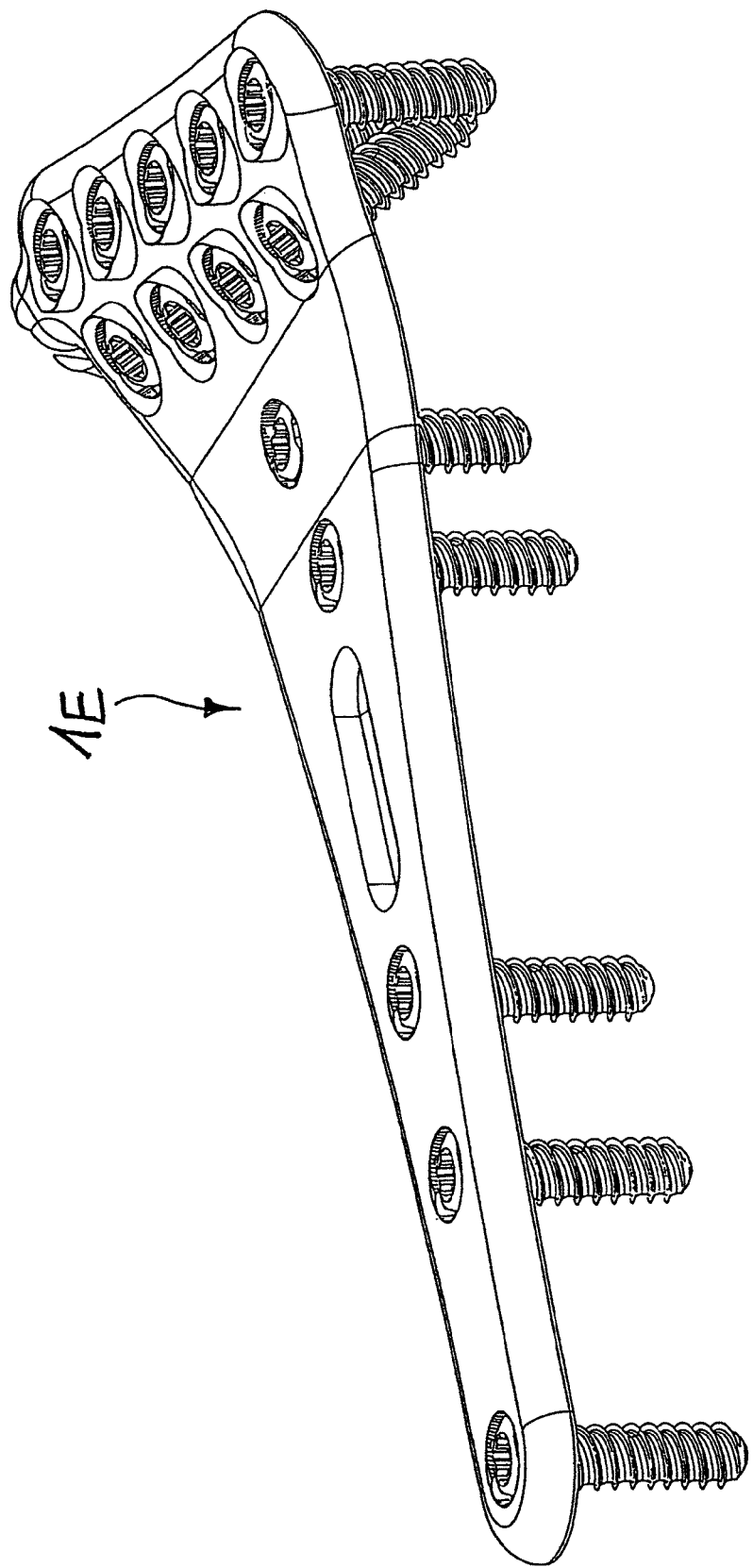
FIG. 12 shows another exemplary embodiment of a bone plate according to the invention which is suitable, e.g., for treating fractures in the area of the distal radius.

FIG. 12 shows another exemplary embodiment of a bone plate 1E according to the invention which is suitable, e.g., for treating fractures in the area of the distal radius. Here again, the partially elevated plate holes of the bone plate can be seen in the area which is provided on the distal end of the radius for attachment close to the wrist. Here again, the same considerations also apply logically with regard to the variability of the design of the bone plate, as already explained in greater detail above on the basis of the exemplary embodiments of the inventive bone plate.

Figure 13:
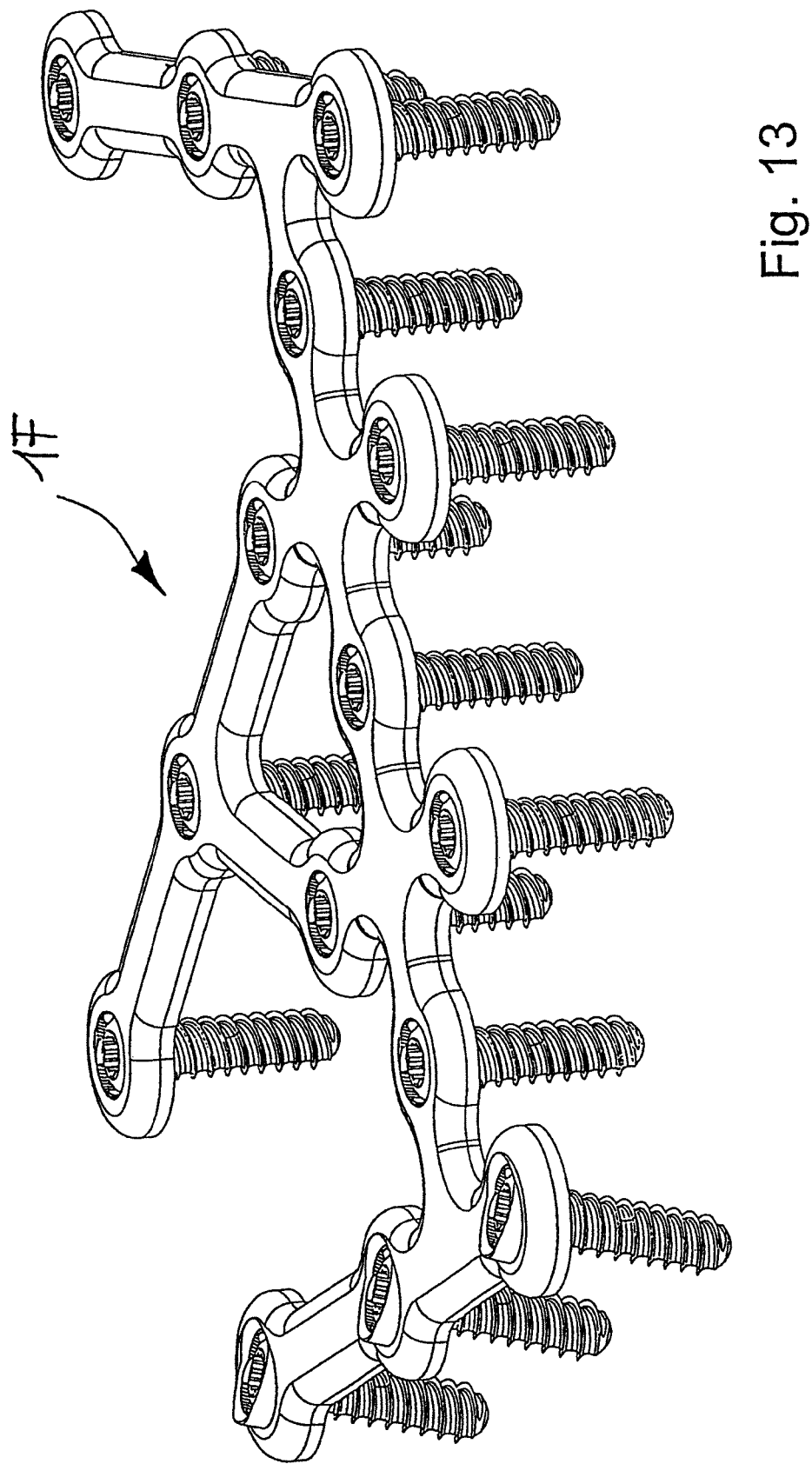
FIG. 13 shows another exemplary embodiment of a bone plate which is suitable for treating fractures of the calcaneus (heel-bone)

Finally, FIG. 13 shows another exemplary embodiment of a bone plate 1F which is suitable for treating fractures of the calcaneus (heel-bone), for example. With regard to this exemplary embodiment of the bone plate, the same considerations also apply logically with respect to the variability of the embodiment of the bone plate.

Essentially any number of variations are conceivable for the exemplary embodiments shown here merely because the bone plates can be optimally tailored to their intended purpose due to the possibility of individual arrangement and alignment of the hole axes, elevations and inclined surfaces.

The inventive bone plate is typically made of a biocompatible material such as titanium or titanium alloys. Bioabsorbable materials such as HA/PLLA (hydroxyapatite/poly(L-lactic acid)), PLLA/PGA (poly(L-lactic acid)), PLLA/PDLLA/TMC (poly(L-lactic acid)/poly-(D,L-lactic acid)/trimethylenecarbonate); PLLA/PDLLA (poly(L-lactic acid)/ poly-(D,L-lactic acid) may also be considered, however, especially when this is possible in terms of the specifications to be met by the bone plate, so that it is then possible to refrain from subsequent removal of the bone plate and the associated negative effects for the patient.

Specific embodiments of a Bone Plate according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. A bone plate comprising:
    at least one plate hole whose hole axis runs obliquely relative to an underside of the plate, the hole axis having an elevation angle ($\epsilon$) relative to a plane of the underside of the plate which is different from 90°, and in which an upper face of the plate runs at least partially non-parallel to the underside of the plate at least in the area around the plate hole, and runs at a right angle to the hole axis,
    wherein the plate hole is configured such that a bone screw, when screwed into the plate hole, is locked in the plate hole at an angle selected from a predetermined angular range around the elevation angle ($\epsilon$) of the hole axis by only cooperation of the plate hole with the bone screw, and without additional auxiliary means, wherein an axis of the bone screw when screwed-in may assume any selected angle within the predetermined angular range;
    the plate further including an elevation formed on an upper face of the plate in the area around the respective plate hole where the axis of the plate hole runs obliquely relative to the underside of the plate; and
    wherein the plate is not sufficiently thick to permit a head of the bone screw to be completely countersunk, wherein the elevation is configured to permit the head of the bone screw to be completely countersunk in the respective plate hole when screwed-in at a selected angle within the predetermined angular range, and wherein the selected angle is different from the elevation angle ($\epsilon$) of the axis of the plate hole.

2. The bone plate according to claim 1, wherein the predetermined angular range around the elevation angle of the bone plate is approximately 15°.

3. The bone plate according to claim 1, comprising multiple plate holes whose hole axis runs obliquely relative to the underside of the plate, wherein both the elevation angle ($\epsilon$) of the hole axis and an azimuth angle or rotational angle in the plane of the underside of the plate, can be determined for each individual plate hole.

4. The bone plate according to claim 1, comprising multiple plate holes having the elevation, wherein at each plate hole having the elevation the elevation is designed and arranged individually.

5. The bone plate according to claim 4, comprising multiple eyes and webs through which the eyes are connected to one another, with the plate having a respective elevation in the area of one or more eyes but not in the area of the webs between the eyes.

6. The bone plate according to claim 1, wherein all plate holes are configured such that during fixation of the plate using bone screws, all the bone screws can be screwed in interorally.

7. The bone plate according to claim 1, wherein a material thickness of the bone plate is in the range of 0.5 mm to 2.5 mm.

8. The bone plate according to claim 1, wherein an inner wall of the plate hole or the plate holes, respectively, is provided with a blocking contour which cooperates with the bone screw, which can be screwed into the respective plate hole such that it can be locked in the plate hole.

9. The bone plate according to claim 8, wherein the blocking contour on the inside wall of the plate hole is configured such that a bone screw, which can be screwed into the plate hole, can be locked by means of a specifically designed clamping surface on the screw head through blocking of the screw head with the blocking contour in the plate hole.

10. The bone plate according to claim 1, wherein the bone plate is made of a biocompatible material.

11. The bone plate according to claim 10, wherein the biocompatible material is a bioabsorbable material.

12. The bone plate according to claim 1, wherein the material thickness of the bone plate is in a range of 0.5 mm to 1.6 mm.

* * * * *